（12）United States Patent
Jones

(10) Patent No.: US 7,696,501 B2
(45) Date of Patent: Apr. 13, 2010

(54) APPARATUS FOR MONITORING ENGINE EXHAUST

(75) Inventor: Michael Lloyd Jones, Buckinghamshire (GB)

(73) Assignee: Hartridge Limited, Buckinghamshire (GB)

( * ) Notice: Subject to any disclaimer, the term of this patent is extended or adjusted under 35 U.S.C. 154(b) by 0 days.

(21) Appl. No.: 11/233,098

(22) Filed: Sep. 23, 2005

(65) Prior Publication Data

US 2006/0065860 A1    Mar. 30, 2006

(30) Foreign Application Priority Data

Sep. 27, 2004    (GB)    .................. 0421469.8

(51) Int. Cl.
*G01N 15/06*    (2006.01)
*G01N 21/00*    (2006.01)
*G01J 5/02*    (2006.01)

(52) U.S. Cl. .................. 250/573; 250/339.13; 356/438

(58) Field of Classification Search ......... 250/573–574, 250/339.13, 364, 373–375, 380, 428; 73/23.31–23.39, 73/23.4, 23.41, 23.42, 31.05; 356/436–439
See application file for complete search history.

(56) References Cited

U.S. PATENT DOCUMENTS 3,306,156 A    2/1967    Glasser et al.
3,906,241 A *  9/1975    Thompson ................... 250/574
5,070,246 A * 12/1991    Durham et al. ............. 250/373
5,512,757 A    4/1996    Cederstrand et al.
5,739,038 A    4/1998    Burrows
5,828,058 A * 10/1998    Yamada ................. 250/227.14
6,396,056 B1 *  5/2002    Lord et al. ............... 250/252.1
6,570,655 B1    5/2003    Shiefer et al.
2002/0026822 A1 *  3/2002    Reading et al. ............ 73/31.05
2003/0225532 A1 * 12/2003    Stedman et al. ............... 702/24

FOREIGN PATENT DOCUMENTS

WO    WO 02/066962 A1    8/2002

* cited by examiner

*Primary Examiner*—Thanh X Luu
(74) *Attorney, Agent, or Firm*—Clark & Brody

(57) ABSTRACT

An apparatus for monitoring the exhaust of an engine includes a flow-through chamber for receiving exhaust, a source of electromagnetic radiation and a detector. The source provides electromagnetic radiation in a range comprising the infrared, visible and ultraviolet wavelengths. The source and a detector are arranged so that radiation passing through the chamber is incident on the detector. An electronic circuit is connected to the detector to provide a signal indicative of the attenuation of the radiation by particles in the exhaust in the chamber. The detector provides respective measures of radiation which it receives for at least two different wavelengths of the radiation, and the electronic circuit provides corresponding electrical signals indicating the attenuation of the two different wavelengths by particles within the exhaust in the chamber. The wavelengths are selected to be those for which the attenuation caused by nitrogen dioxide in the exhaust is substantially the same.

11 Claims, 6 Drawing Sheets

APPARATUS FOR MONITORING ENGINE EXHAUST

TECHNICAL FIELD

This invention relates to the an of apparatus for monitoring the exhaust of internal combustion engines.

BACKGROUND OF THE INVENTION

The present invention is directed to apparatus for monitoring engine exhaust, comprising a chamber for receiving such exhaust, an inlet of the chamber adapted to be connected to the engine exhaust and an outlet from the chamber to enable exhaust to escape therefrom, so that exhaust from the engine can flow through the chamber continuously, a source of electromagnetic radiation which is of a wavelength within a range comprising the infrared, visible and ultraviolet wavelengths, detector means which detects the amount of such radiation it receives, the source and the detector being so arranged that radiation emitted by the source is received by the detector after the radiation has passed through the chamber, and electrical means connected to the detector to provide an electrical signal which is indicative of the attenuation of the radiation as a result of the presence of particles within the exhaust in the chamber, in which the detector means is such as to be able to provide respective different measures of radiation which it receives for at least two different wavelengths of such radiation, and the electrical means are such as to provide respective electrical signals which are indicative of the attenuation of the radiation, as a result of the presence of particles within the exhaust in the enclosure, for the said at least two different wavelengths.

One shortcoming of such apparatus is that it takes no account of the effects of nitrogen dioxide present in the exhaust. This is a brown gas which absorbs radiation in much of the visible and UV range. Its concentration may fluctuate, and its opacity as a function of wavelength is not simple. Furthermore, oxidation catalysts now fitted to many vehicles increases the amount of nitrogen dioxide present in the engine exhaust as much as tenfold. At the same time, engines are becoming more efficient, so that soot concentration levels have become low. These things very much increase the adverse effect of nitrogen dioxide on the apparatus.

SUMMARY OF THE INVENTION

The present invention seeks to overcome this problem.

Accordingly, the present invention is directed to apparatus having the construction set out in the opening paragraph of the present specification in which the said at least two different wavelengths are wavelengths at which the attenuation of electromagnetic radiation caused by the presence of nitrogen dioxide in the exhaust is substantially the same.

This provides the advantage that the apparatus will indicate if the particle size is sufficiently small to make a difference in the attenuation of the electromagnetic radiation at the respective different wavelengths, independently of the nitrogen dioxide content of the exhaust. This in turn is significant from the point of view of harmful pollution because particles of a small size are more readily absorbed by the body, especially lung tissue, than particles of a larger size.

Preferably, one of the said two different wavelengths is substantially 300 nm, and the other is substantially 500 nm. This benefits from a relatively large difference between the wavelengths, to increase the sensitivity of the apparatus to the presence of small soot particles within the exhaust.

Preferably, the detector means are such as to be capable of providing different measures of radiation which it receives for more than two different wavelengths, preferably three. The third wavelength is preferably that for red light, more preferably substantially 680 nm, at which the attenuation caused by the presence of nitrogen dioxide is substantially negligible. This enables the apparatus to give a clearer assessment of one dominant particle size in the exhaust, without being unduly adversely affected by nitrogen dioxide.

Preferably, there are at least two detectors in the detector means for each different wavelength that is detected. This reduces the likelihood of spurious measurements from inadequately mixed exhaust.

Preferably, blowers are provided to blow a curtain of air or other gas across the operative faces of the source and/or the detector means to reduce the extent to which they might become permanently marked by materials within the exhaust.

This reduces the likelihood of any error owing to such a mark. Preferably, the operative faces of the source and/or the detector means are flat and/or smooth to facilitate the passage of such a curtain of air or other gas.

Preferably, the light source is a single broadband source which emits electromagnetic energy across the range of wavelengths which comprises the said at least two different wavelengths.

It is desirable for the electrical means to comprise an Analog to Digital Converter to convert signals obtained from the detector means to a stream of pulses providing respective measures of the attenuation of the electromagnetic energy at the said at least two different wavelengths at regular intervals in real time.

Preferably, the electrical means calculate the k value for each sensor of the detector means given by the equation:

$$k = 1/L * \log_e(1 - 0.01 * N)$$

where L is the smoke column length, being the effective optical path length for the electromagnetic radiation through exhaust filled regions in passing from the source to the detector means, and N is the opacity for that sensor given by the equation:

$$N = 100 * (V - V_o)/V_{100} - V_o)$$

V being the value of the signal from the sensor at any given time, $V_{100}$ being the reading from the sensor when the chamber is totally opaque, or when there is no electromagnetic radiation passing through it, and $V_o$ being the reading from the sensor for full transmission when there is no exhaust in the chamber.

The present invention extends to a method of monitoring engine exhaust comprising passing the exhaust through a chamber, directing electromagnetic radiation through the exhaust in the chamber, and providing a measure of the attenuation of such radiation for at least two different wavelengths thereof at which the attenuation of such radiation caused by the presence of nitrogen dioxide in the exhaust is substantially the same.

BRIEF DESCRIPTION OF THE DRAWINGS

An example of apparatus embodying the present invention will now be described by way of example with reference to the accompanying drawings in which:

FIG. 1b shows in greater detail a part of the apparatus shown in FIG. 1 viewed in the direction indicated by the arrow 'A' shown in FIG. 1;

DETAILED DESCRIPTION OF THE PREFERRED EMBODIMENTS

Figure 1:
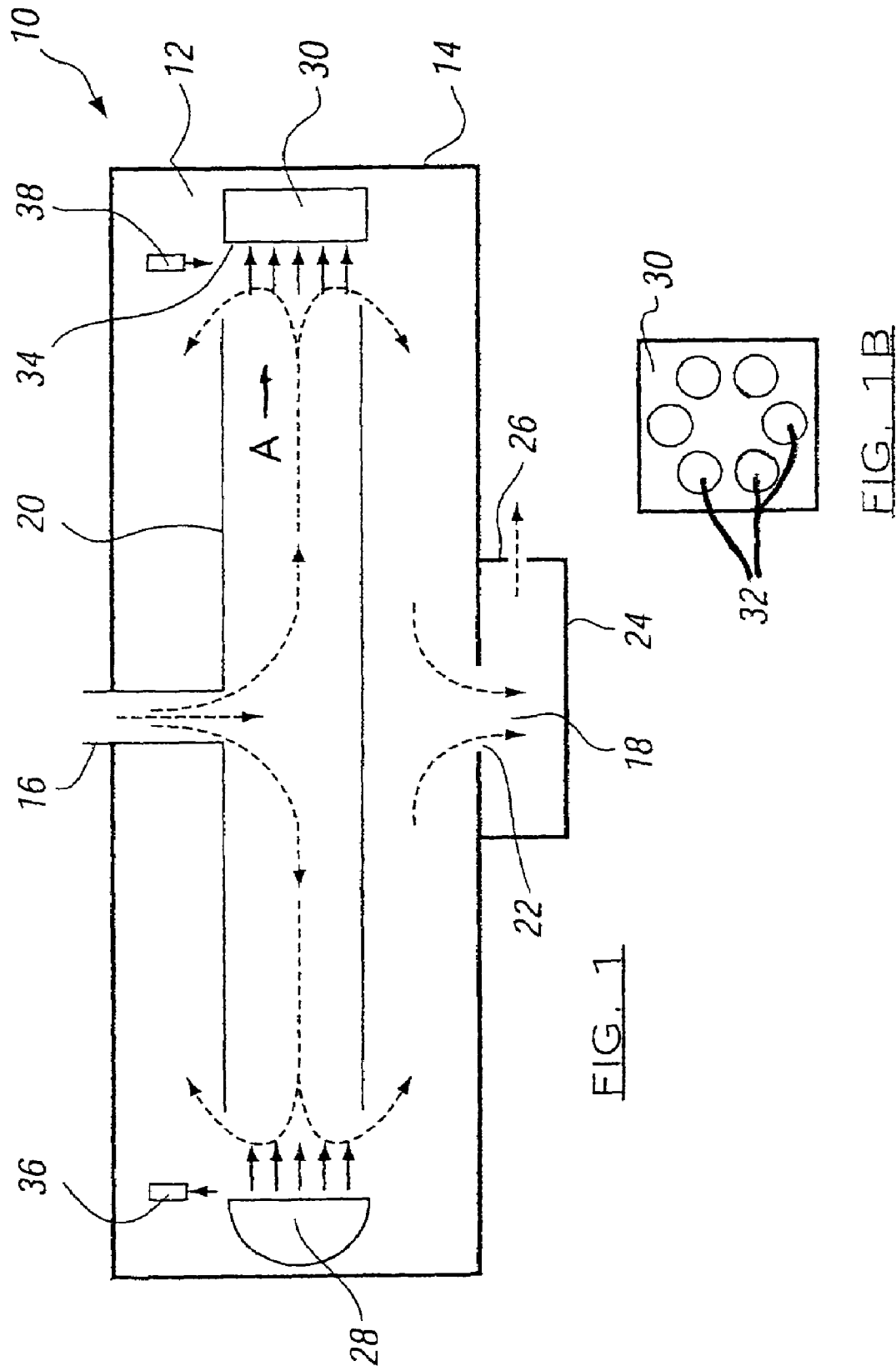
FIG. 1 shows a diagram of the apparatus and its interior.

The apparatus 10 shown in FIG. 1 comprises an enclosure 12 defined by a generally cylindrical closed housing 14, having an inlet 16 positioned halfway along the housing 14, and which is adapted to be connected to an engine exhaust, and an outlet 18, which is also positioned halfway along the length of the housing 14, but which is diametrically opposite the inlet 16. The outlet 18 is for the extraction of waste exhaust/airmix from the enclosure 12. The inlet 16 is connected to feed exhaust through a wall of a cylinder 20, which defines a measuring chamber, at a position equidistant from the ends thereof. The cylinder 20 is open at both ends. As a result a path is provided for exhaust which starts at the inlet 16, progresses in both directions therethrough outwardly towards the respective ends of the cylinder 20 close to the closed ends of the housing 14, back along the enclosure 12 towards a position halfway along the housing 14 around the outside of the cylinder 20 and thence out through the outlet 18.

The outlet 18 comprises a simple aperture 22 within the side wall of the housing 14, and a hollow box construction 24 mounted around that aperture 22, the box 24 being provided with a further aperture 26 in its side. The box 24 houses an extractor fan (not shown) to expel exhaust/airmix through the aperture 26.

A source of white light in the form of a tungsten lamp 28 is seated in the enclosure 12 on the interior of one of the ends of the housing 14 and is oriented as to direct radiation along the interior of the cylinder 20.

Seated on the interior of the other end of the housing 14 is a detector block 30 having a multiplicity of sensors 32 in an operative face 34 of the block 30. This operative face 34 is directed to receive radiation which has been emitted from the lamp 28 and which has passed through the interior of the cylinder 20.

Each sensor 32 is selectively sensitive to a particular wavelength of electromagnetic radiation. Thus, two may be selectively sensitive to radiation of the wavelength 300 nm, two may be selectively sensitive to radiation of wavelength 500 nm, and two may be selectively sensitive to red light of wavelength 680 nm. The selective sensitivity may be effected by means of respective optical filters in the operative face 34.

Blocks 36 and 38 are mounted within the enclosure 12 to direct curtains of air across the operative faces of the source 28 and detector block 30, respectively. The spacing between the air curtains defines the effective optical path length for the measurement of opacity, and it will be appreciated that this somewhat exceeds the length of the cylinder 20. It will also be appreciated that the introduction of air by the blocks 36 and 38 significantly dilutes the exhaust with clean air before it exits through the aperture 26.

Figure 2:
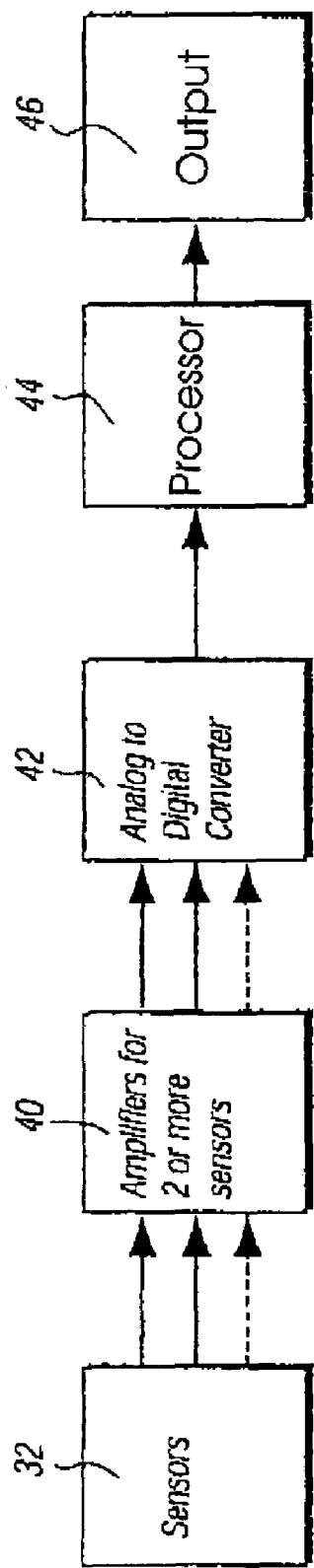
FIG. 2 shows a diagram of circuitry used with the apparatus shown in FIG. 1.

Circuitry is provided for the sensors 32 as shown in FIG. 2. This comprises a plurality of amplifiers 40, connected respectively to the sensors 32. The outputs from the amplifiers 40 are connected to an Analog to Digital Converter 42, an output of the Analog to Digital Converter is connected to an input of a processor 44 which in turn provides output signals at its output 46. These signals indicate in digital form the respective outputs of the sensors 32 every 50 ms.

Figure 3:
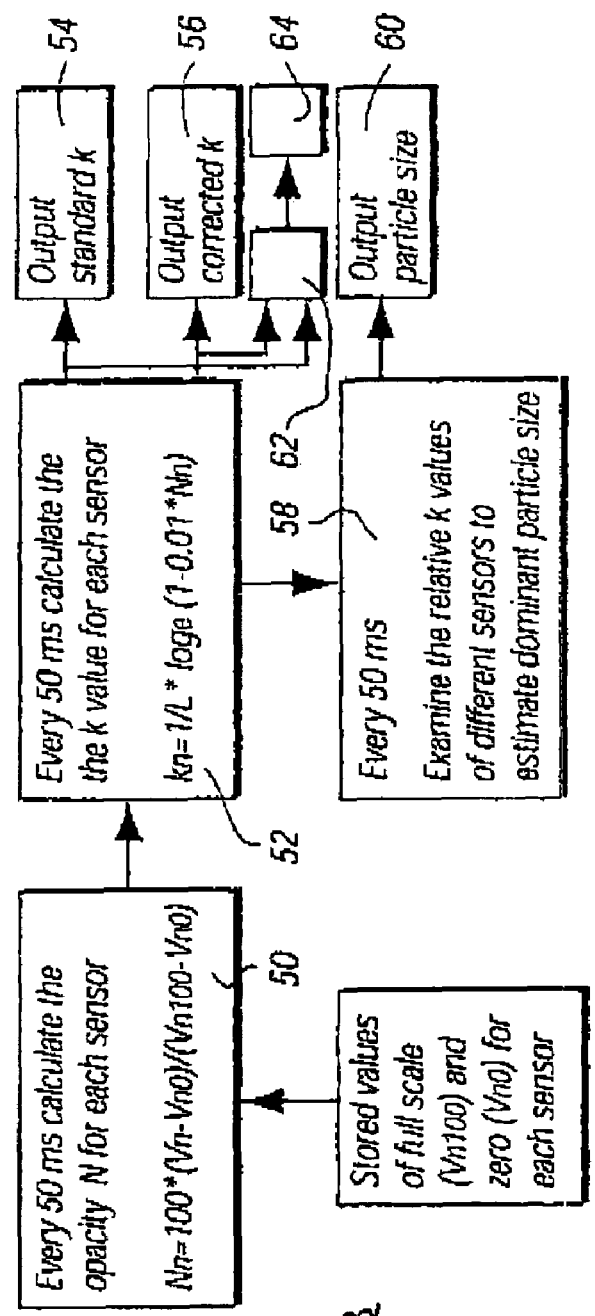
FIG. 3 shows a diagram of the steps taken in the programme executed by a processor in the circuitry shown in FIG. 2.

The processor 44 is programmed to perform the steps set out in FIG. 3. Thus, at step 50, every 50 ms it cycles through the digital values of the sensor outputs and, during each cycle calculates the opacity N for each sensor n given by the equation:

$$N_n = 100 * (V_n - V_{no}) / V_{n100} - V_{no}).$$

To enable it to complete this calculation, it receives stored values held in the processor 44 for each sensor 32 of the end of scale values $V_{no}$, being the digital output from the sensor 32 when there is no exhaust in the chamber and the source 28 is switched on, and at the other end of the scale, the value of $V_{n100}$ for the sensor n when there is no light reaching the sensor n, for example when the lamp 28 is switched off. (These values are created and stored in the processor 44 during a calibration procedure).

At step 52, the processor 44 calculates the k value for each sensor n as given by the equation:

$$k_n = 1/L * \log_e(1 - 0.01 * N_n).$$

This provides a stream of signals representing the k value for green light at output 54 every 50 ms, and a corresponding stream at output 56 for a combination of all the k factors weighted towards those for shorter wavelengths. This output 54 may be considered the output for k standard, and the output 56 for k corrected, since it takes account of particles which might be invisible to green light.

The processor 44 is further programmed to execute step 58 which examines the relative k values of the different sensors to provide an estimate of the dominant particle size on the basis of the different k values. These further results are provided as a stream of output signals at an output 60 which gives the dominant particle size. Outputs 54 and 56 are further processed at step 62 to provide a stream of weighted k values given by the equation:

$$k_w = w(k_c - k_s) + k_s$$

in which $k_w$ is the weighted k value, w is the weighting factor (for example the value 5), $k_c$ is the corrected k value and $k_s$ is the standard k value. The stream of $k_w$ values is provided at output step 64.

The signals from all the outputs 54, 56, 60 and 64 may either be stored for subsequent use or fed directly to a screen via appropriate screen drivers to provide a graph of the values of the outputs plotted against time.

Figure 4:
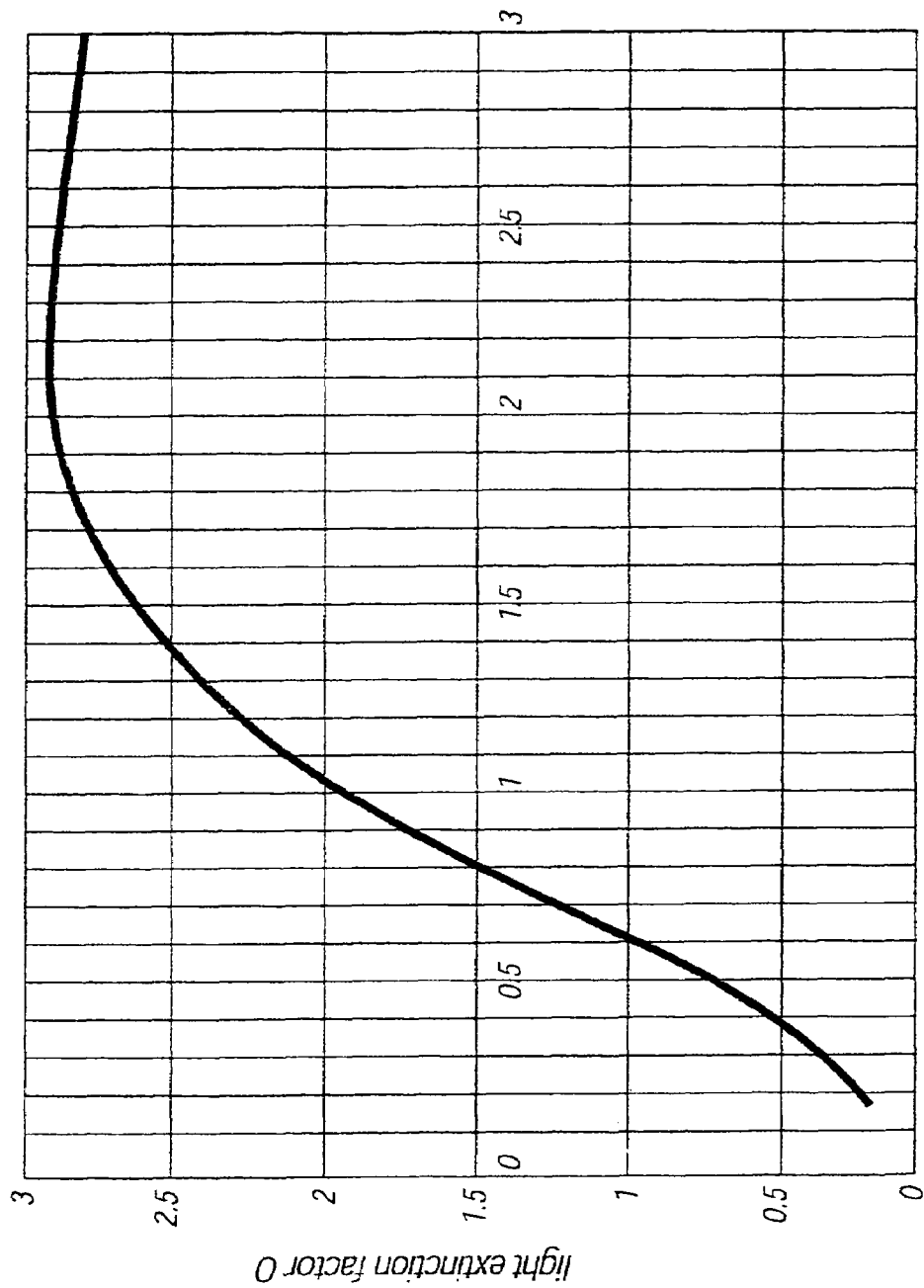
FIGS. 4 to 8 show respective different explanatory graphs.

FIG. 4 shows the Mie theory extinction graph for absorbing particles. This shows a light extinction factor Q (a value which is normalised as regards concentration of particles and the radiation wavelength) plotted against the particle, the parameter of which is given by the value of the natural constant π multiplied by the diameter d of the particle divided by the wavelength λ of the radiation.

Figure 5:
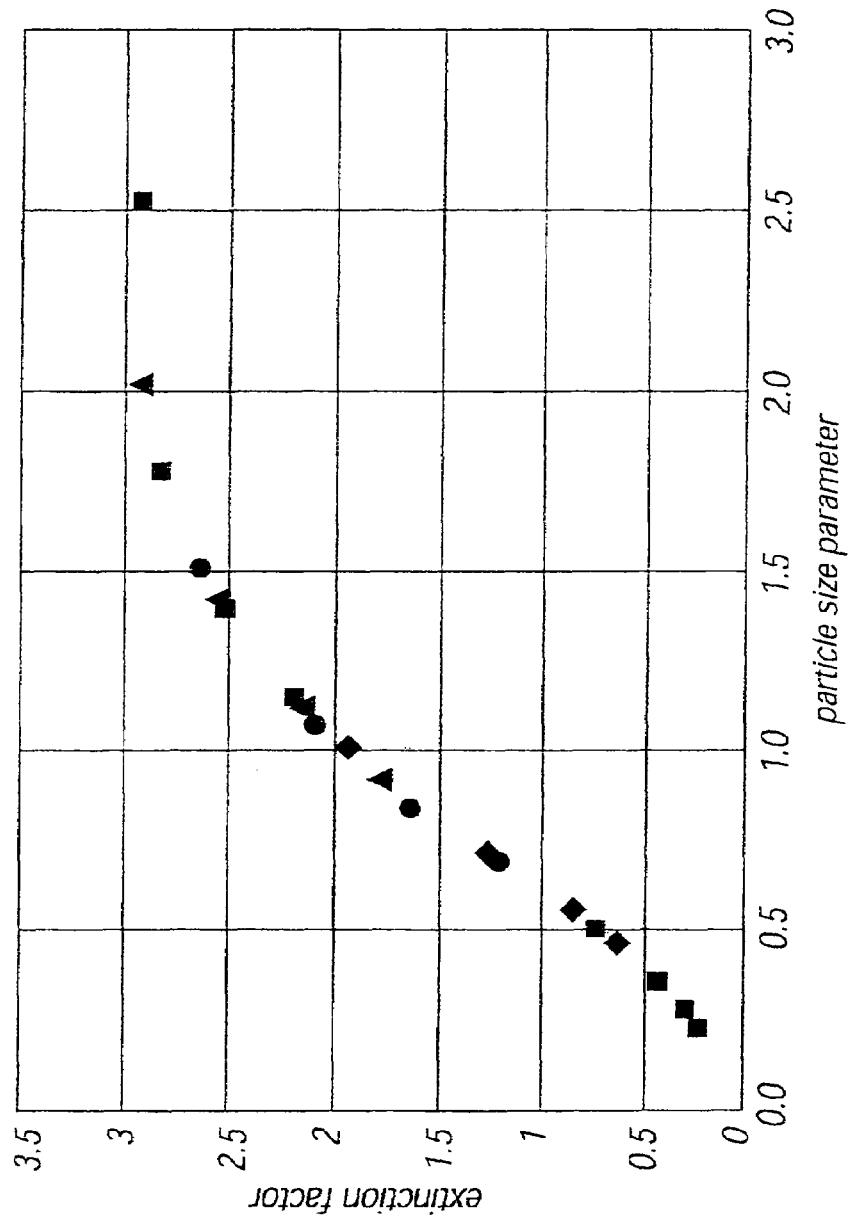

FIG. 5 shows particular values on the extinction curve. Thus, the small squares show the positions on the curve for particles of size 50 nm for the wavelengths 680 nm (corresponding to red light), 560 nm (corresponding to green light), 440 nm (corresponding to blue light), and 310 nm (corresponding to ultra-violet light), progressing from the left to the right of the diagram. The diamond shapes show these values for particles of 100 nm, the circle for particles of 150 nm, the triangles for particles of size 200 nm and the large squares for particles of size 250 nm. It will be seen from this diagram that there is very little difference in the extinction factor for particles the size of which, relative to the wavelength which is considered, is large. Once the particle size is small compared to the wavelength considered, the extinction factor is very low. The greater the spread in the readings for the different sensors for the apparatus shown in FIG. 1, the closer is the particle size parameter to the range 0.5 to 1.0, where the divergence is greatest.

Figure 6:
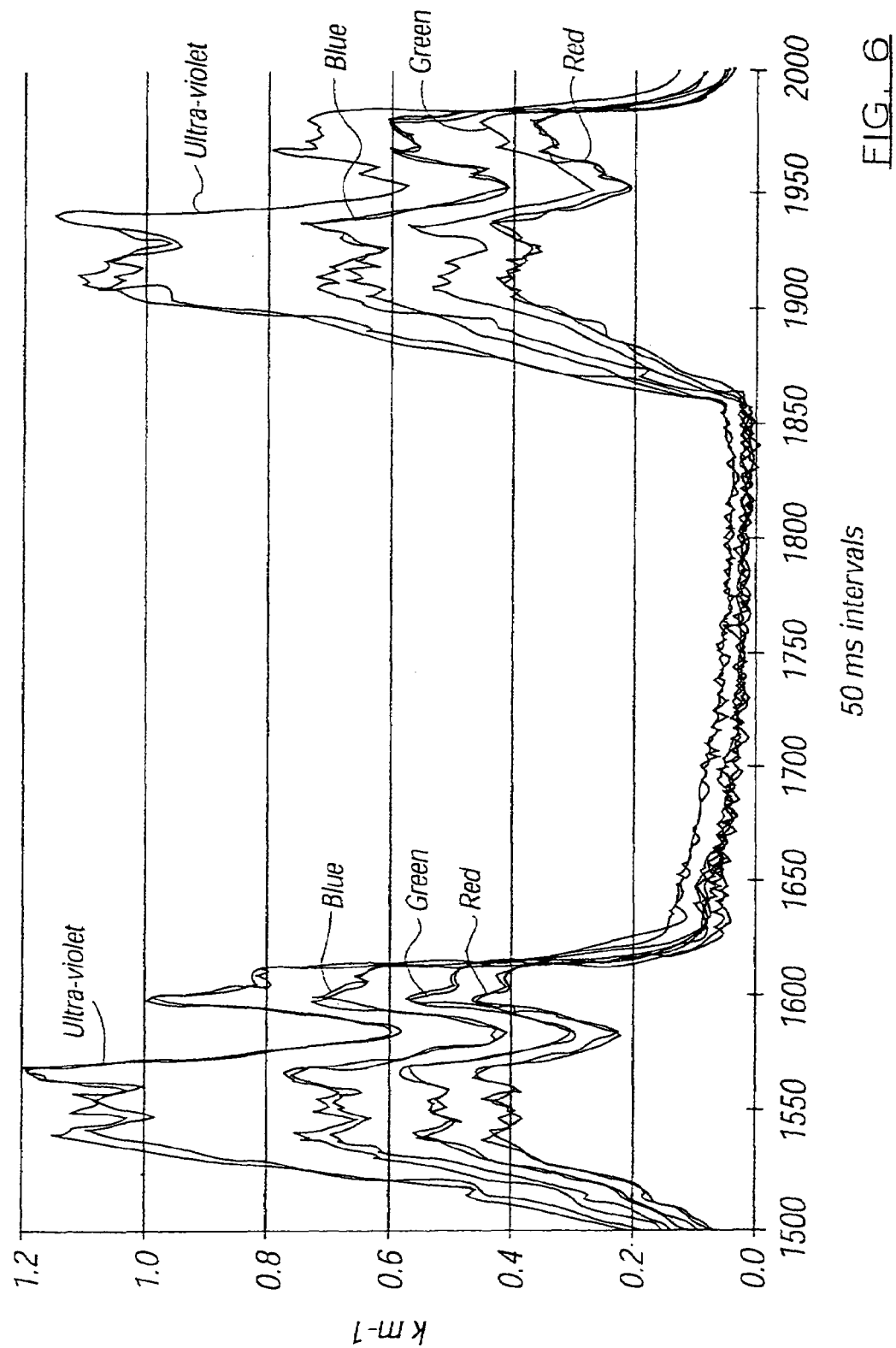

FIG. 6 shows the k values with respect to time as given by the apparatus shown in FIG. 1 with the latter being connected to the exhaust of a diesel engine having a common rail. The peaks represent free accelerations and the spacing for the different colours indicates a dominant particle size of between 100 and 150 nm.

Figure 7:
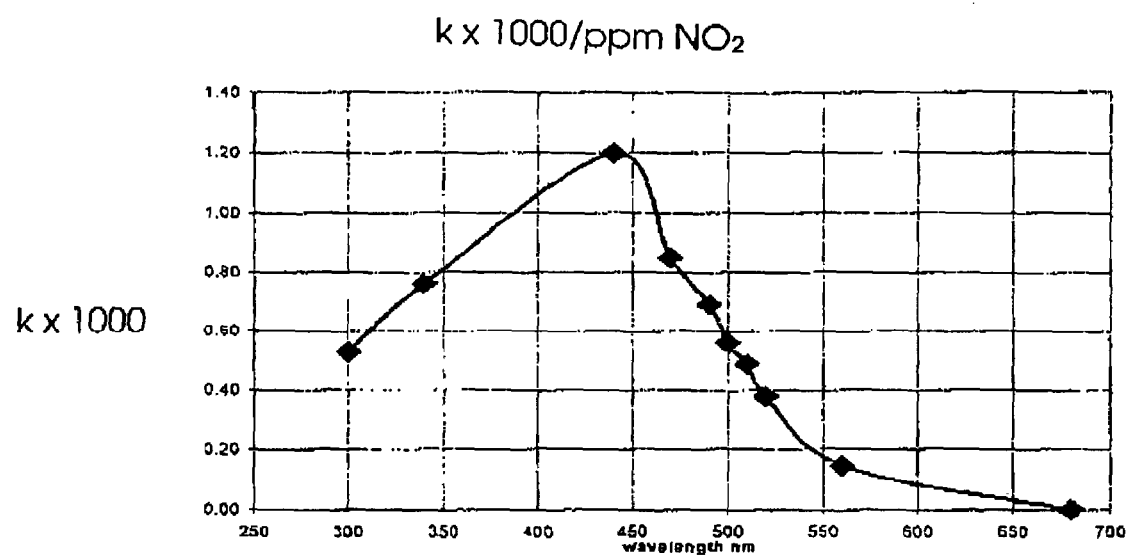

FIG. 7 shows a plot of the k value as a function of wavelength of light being attenuated by the presence of 150 parts per million of nitrogen dioxide in nitrogen gas. It will be noted that at the red end of the spectrum, where the wavelength is long, there is substantially no attenuation. This means that red light, with a wavelength of substantially 680 nm, is substantially unaffected by nitrogen dioxide. At the same time, because of the shape of the curve, being very roughly an inverted V for the range 300 nm to 500 nm, there are two different wavelengths for which the attenuating effect of nitrogen dioxide is substantially the same. For maximum resolution, therefore, selection of 300 nm and 500 nm as the two different wavelengths for the illustrated apparatus to work in accordance with the invention is desirable.

Figure 8:
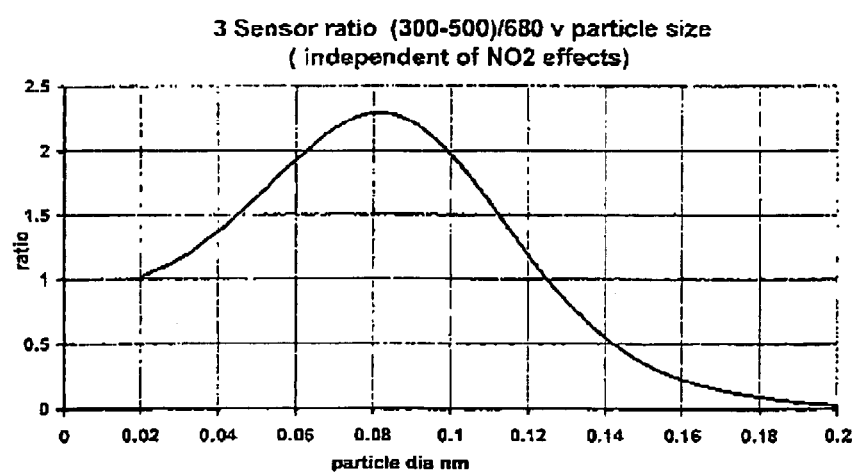

FIG. 8 shows the ratio $(k_{300}-k_{500})/k_{680}$ as a function of particle size, where $k_n$ is the k value for wavelength n nm, the ratio being substantially independent of the concentration of nitrogen dioxide in the exhaust, and substantially independent of particle concentration. This function may be used to determine the dominant particle size in step 58.

It will thereby be appreciated that the apparatus shown in FIG. 1 provides an indication of the density of particles in the exhaust and an indication of the dominant particle size in that exhaust, substantially independently of the nitrogen dioxide content of the exhaust. A given threshold value for these readings, for example a given threshold value for the output signals of the output 64 may be agreed to determine whether or not the engine passes or fails an emissions test.

The apparatus shown in FIG. 1 may be modified in various different ways without taking the resulting construction outside the scope of the present invention. For example, there may be fewer sensors 32, perhaps as low as only two sensors providing measures of attenuation at different wavelengths. Conversely, there may be more than the six sensors shown in FIG. 1b, with a cluster of sensors on each wavelength to enable a better mean value to be obtained for that wavelength. The path of the exhaust may be in a meandering fashion instead of the longitudinal contra-flow arrangement shown in FIG. 1.

The illustrated apparatus can be readily mounted on the rear of a vehicle, with the inlet 16 attached via a flexible hose (not shown) to the vehicle engine exhaust. It is suitable for in-service particulate testing of diesel vehicles, and can be used to assess oil burning in gasoline vehicles. The electrical means may be provided with the apparatus 10 or at least partially by a portable computer. The apparatus has a rapid response enabling it to measure transient effects.

All the output values at outputs 54, 56, 60 and 64 can be smoothed by processing them in accordance with the equation:

$$k_{av}.0.9k_{old}+0.1k_{new}$$

in which $k_{new}$ is the latest value, $k_{old}$ is the last calculated averaged or smoothed value, and $k_{av}$ is the averaged or smoothed k value. Peak values may be captured for transient tests.

I claim:

1. Apparatus for monitoring engine exhaust, comprising
a chamber for receiving such exhaust, an inlet of the chamber adapted to be connected to the engine exhaust and an outlet from the chamber to enable exhaust to escape therefrom, so that exhaust from the engine can flow through the chamber continuously,
a source of electromagnetic radiation which is of a wavelength within a range comprising the infrared, visible and ultraviolet wavelengths,
a detector which detects the amount of such radiation it receives, the source and the detector being so arranged that radiation emitted by the source is received by the detector after the radiation has passed through the chamber, and
electrical circuitry connected to the detector to provide an electrical signal which is indicative of the attenuation of the radiation as a result of the presence of particles within the exhaust in the chamber, in which the detector is such as to be able to provide respective different measures of radiation which it receives for at least two different wavelengths of such radiation, and the electrical circuitry is such as to provide respective electrical signals which are indicative of the attenuation of the radiation, as a result of the presence of particles within the exhaust in the chamber, for the said at least two different wavelengths,
wherein the said at least two different wavelengths are wavelengths at which the attenuation of electromagnetic radiation caused by the presence of nitrogen dioxide in the exhaust is substantially the same to permit detection of said presence of said particles independent of the concentration of nitrogen dioxide in the exhaust, and wherein the detector is capable of providing different measures of radiation which it receives for three different wavelengths, one of said three different wavelengths being red light.

2. Apparatus according to claim 1, wherein one of the said two different wavelengths is substantially 300 nm, and the other is substantially 500 nm.

3. Apparatus according to claim 1, wherein the third wavelength is substantially 680 nm.

4. Apparatus according to claim 1, wherein there are at least two sensors in the detector for each different wavelength that is detected.

5. Apparatus according to claim 1, wherein a blower is provided to blow a curtain of gaseous material across the operative face of the source to reduce the extent to which it might become permanently marked by materials within the exhaust.

6. Apparatus according to claim 5, wherein the operative face of the source is flat to facilitate the passage of such a curtain of air or other gas.

7. Apparatus according to claim 1, wherein the source is a single broadband source which emits electromagnetic energy across the range of wavelengths which comprises the said at least two different wavelengths.

8. Apparatus according to claim 1, wherein the electrical circuitry comprises an Analog to Digital Converter to convert signals obtained from the detector to a stream of pulses providing respective measures of the attenuation of the electromagnetic energy at the said at least two different wavelengths at regular intervals in real time.

9. Apparatus according to claim 1, wherein the electrical circuitry calculates the k value for each sensor of the detector given by the equation:

$$k = 1/L * \log_e(1 - 0.01 * N)$$

where L is the smoke column length, being the effective optical path length for the electromagnetic radiation through exhaust filled regions in passing from the source to the detector, and N is the opacity for that sensor given by the equation:

$$N = 100 * (V - V_o) / V_{100} - V_o)$$

V being the value of the signal from the sensor at any given time, $V_{100}$ being the reading from the sensor when the chamber is totally opaque, or when there is no electromagnetic radiation passing through it, and $V_0$ being the reading from the sensor for full transmission when there is no exhaust in the chamber.

10. A method of monitoring engine exhaust comprising:

passing the exhaust through a chamber, directing electromagnetic radiation through the exhaust in the chamber, and providing a measure of the attenuation of such radiation for at least two different wavelengths thereof at which the attenuation of such radiation caused by the presence of nitrogen dioxide in the exhaust is not substantially negligible but is substantially the same for the two different wavelengths to permit detection of the presence of particles independent of the concentration of nitrogen dioxide in the exhaust.

11. A method of monitoring engine exhaust according to claim 10, wherein:

said chamber is configured for receiving such exhaust, an inlet of the chamber adapted to be connected to the engine exhaust and an outlet from the chamber to enable exhaust to escape therefrom, so that exhaust from the engine can flow through the chamber continuously, said directing step comprises utilizing a source of electromagnetic radiation which is of a wavelength within a range comprising the infrared, visible and ultraviolet wavelengths, said providing step comprises utilizing a detector which detects the amount of such radiation it receives, the source and the detector being so arranged that radiation emitted by the source is received by the detector after the radiation has passed through the chamber, and said providing step further comprises utilizing electrical circuitry connected to the detector to provide an electrical signal which is indicative of the attenuation of the radiation as a result of the presence of particles within the exhaust in the chamber, in which the detector is such as to be able to provide respective different measures of radiation which it receives for at least two different wavelengths of such radiation, and the electrical circuitry is such as to provide respective electrical signals which are indicative of the attenuation of the radiation, as a result of the presence of particles within the exhaust in the chamber, for the said at least two different wavelengths, wherein the said at least two different wavelengths are wavelengths at which the attenuation of electromagnetic radiation caused by the presence of nitrogen dioxide in the exhaust is substantially the same, and wherein the detector is capable of providing different measures of radiation which it receives for three different wavelengths, one of said three different wavelengths being red light and one of the said two different wavelengths is substantially 300 nm, and the other is substantially 500 nm.

* * * * *